(12) United States Patent
Grubis (10) Patent No.: US 10,368,748 B2
(45) Date of Patent: **\*Aug. 6, 2019**

(54) SYSTEM AND METHOD OF EVALUATING AN ASSOCIATION BETWEEN A WIRELESS SENSOR AND A MONITORED PATIENT

(71) Applicant: General Electric Company, Schenectady, NY (US)

(72) Inventor: Matthew George Grubis, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/238,366

(22) Filed: Aug. 16, 2016

(65) Prior Publication Data

US 2016/0353993 A1 Dec. 8, 2016

Related U.S. Application Data

(63) Continuation of application No. 14/066,004, filed on Oct. 29, 2013, now Pat. No. 9,443,059.

(51) Int. Cl.
*A61B 5/04* (2006.01)
*A61B 5/00* (2006.01)
(Continued)

(52) U.S. Cl.
CPC ........ *A61B 5/0024* (2013.01); *A61B 5/02055* (2013.01); *A61B 5/0402* (2013.01); *A61B 5/04012* (2013.01); *A61B 5/0476* (2013.01); *A61B 5/7221* (2013.01); *A61B 5/742* (2013.01); *A61B 5/746* (2013.01);
(Continued)

(58) Field of Classification Search
CPC .............. A61B 5/0024; A61B 5/02055; A61B 5/04012; A61B 5/021
See application file for complete search history.

(56) References Cited

U.S. PATENT DOCUMENTS 4,718,081 A * 1/1988 Brenig .................. H04W 36/30
455/438
6,661,345 B1 12/2003 Bevan et al.
(Continued)

FOREIGN PATENT DOCUMENTS

WO 2012123705 A1 9/2012
WO 2013036379 A1 3/2013

OTHER PUBLICATIONS

International Search Report and Written Opinion issued in corresponding international application No. PCT/US2014/049133 dated Nov. 28, 2014.

*Primary Examiner* — Catherine M Voorhees
*Assistant Examiner* — Natasha Patel
(74) *Attorney, Agent, or Firm* — Andrus Intellectual Property Law, LLP (57) ABSTRACT

Systems and methods of evaluating an association between a wireless sensor and a monitored patient include a plurality of peripheral electronic devices each having a wireless communication system and a sensor. A processor receives measured physiological parameter data from the peripheral electronic devices and establishes an association status between each of the peripheral electronic devices and the monitored patient based upon identified characteristics in the physiological parameter data.

20 Claims, 5 Drawing Sheets

(51) Int. Cl.
  *G06F 19/00* (2018.01)
  *A61B 5/0205* (2006.01)
  *A61B 5/0402* (2006.01)
  *A61B 5/0476* (2006.01)
  *G16H 40/63* (2018.01)
  *A61B 5/021* (2006.01)
  *A61B 5/024* (2006.01)
  *A61B 5/08* (2006.01)
  *A61B 5/145* (2006.01)

(52) U.S. Cl.
  CPC ......... *G06F 19/3418* (2013.01); *G16H 40/63* (2018.01); *A61B 5/021* (2013.01); *A61B 5/024* (2013.01); *A61B 5/0816* (2013.01); *A61B 5/14542* (2013.01)

(56) References Cited

U.S. PATENT DOCUMENTS

| | | | | |
|---|---|---|---|---|
| 8,430,817 | B1* | 4/2013 | Al-Ali | A61B 5/7221 128/920 |
| 2002/0087194 | A1* | 7/2002 | Russell | A61N 1/39 607/5 |
| 2008/0154503 | A1* | 6/2008 | Wittenber | A61B 5/02055 701/300 |
| 2009/0186577 | A1* | 7/2009 | Ross | H04Q 9/00 455/41.2 |
| 2011/0149759 | A1* | 6/2011 | Jollota | A61B 5/0024 370/252 |
| 2013/0304142 | A1* | 11/2013 | Curtin | A61N 1/3975 607/5 |
| 2014/0171749 | A1* | 6/2014 | Chin | A61B 5/7221 600/300 |

* cited by examiner

SYSTEM AND METHOD OF EVALUATING AN ASSOCIATION BETWEEN A WIRELESS SENSOR AND A MONITORED PATIENT

CROSS REFERENCE TO RELATED APPLICATION

This application is continuation of U.S. application Ser. No. 14/006,004, filed Oct. 29, 2013, which application was published on Apr. 30, 2015, as U.S. Publication No. US20150119773, which application is incorporated herein by reference in its entirety.

BACKGROUND

The present disclosure is related to the field of wireless sensing. More specifically, the present disclosure is related to evaluating an association between a wireless sensor and a monitored patient.

Monitoring vital signs is an important part of patient care as the general or particular health of the patient is determined, in part, through measurement and interpretation of key physiological indicators. Well-known parameters of patient health include blood pressure, hemoglobin saturation ($SPO_2$), and features of the electrocardiogram (ECG). However, the utilization of physiological instrumentation to obtain these measurements at the bed side of a patient also possess well-known burdens to the clinical environment. The presence of cables, catheters, and tubing connecting the patient and sensors to the instrumentation configured to provide all monitoring or therapeutic care can diminish productivity and the quality of patient care. For example, rotating a patient to alleviate bed sores or ambulating about the room can be problematic if one is saddled with tethered devices. Procedural delays stemming from cable management also contribute to a great percentage of time dedicated to routine, mundane tasks not directly related to treatment of the patient's illness.

Wireless communication technology leveraged to patient monitoring may at least mitigate some of the problems associated with cable clutter and device management. With instrumentation becoming wireless, the management of such devices is eased. In addition, wireless instrumentation/devices greatly reduce the burden associated with cable management.

Wireless patient monitoring networks, however, bring new problems that need to be addressed for proper implementation of a monitoring regime. In many instances, whether using a wireless monitoring system or a wired system, elements of the system communicate with at least one central management device. In the hospital environment, this management device is often used to relay monitored information to an infrastructure that allows health care professionals to analyze the monitored information from an outside location (e.g. a nurse station). In other wireless systems, the management device may be integrated with a central processing unit that analyzes the incoming device information. When cables are removed from these devices, a user of the system can no longer safe guard that the devices are properly connected to the patient to be monitored by the management device by simply ensuring that the cables extend from the management device to the correct patient. That is, without cables, a health care provider or other operator lacks the visual cues associated with cables to assure that the sensing devices are properly connected to the proper patient to be monitored by the management device. Alternatively, as wireless sensing systems proliferate in a care setting, wireless sensing devices may inadvertently become communicatively connected with a management device associated with another patient. Again, without the visual cues of the cable, a healthcare provider or other operator lacks a tool for fast and accurate confirmation that the management device is receiving physiological data from a specified patient and that patient only.

BRIEF DISCLOSURE

An exemplary embodiment of a wireless system includes a plurality of peripheral electronic devices each having a wireless communication system and a sensor. The sensors are configured to measure a physiological parameter of a monitored patient. A hub includes a wireless communication system. The hub is in wireless communication with one or more of the peripheral electronic devices. A processor is configured to receive measured physiological parameter data from the peripheral electronic devices. The processor is configured to identify characteristics of the physiological parameter data associated with the monitored patient. The processor is further configured to establish an association status between each of the peripheral electronic devices and the monitored patient based upon the identified characteristics.

A non-limiting exemplary embodiment of a wireless system includes a plurality of peripheral electronic devices each having a wireless communication system and a sensor. The sensors are configured to each obtain a signal out of a plurality of signals. A hub includes a wireless communication system. The hub is in wireless communication with one or more of the plurality of peripheral electronic devices. A processor is configured to receive at least one input to register each of the plurality of peripheral electronic devices. The processor is configured to receive the plurality of signals from the peripheral electronic devices. The processor is configured to derive at least one association attribute value from the received plurality of signals. The processor is configured to derive a confidence value indicative an association status between a registration of each of the peripheral electronic devices and the at least one association attribute value.

An exemplary non-limiting embodiment of a method of evaluation an association between each of a plurality of wireless sensors configured to obtain physiological data in a monitored patient includes registering the plurality of wireless sensors to the monitored patient with a processor. The processor is configured to receive the physiological data from the plurality of wireless sensors through a hub having a wireless communication system in communication with one or more of the plurality of wireless sensors. The physiological data is received at the processor from the plurality of wireless sensors. At least one association attribute value of a plurality of association attribute values is derived by processing the received physiological data. At least one system attribute value is received as at least one association attribute value of the plurality of association of attribute values. Each of the plurality of association attribute values are weighted. A confidence value is derived from the weighted plurality of association attribute values for each of the plurality of wireless sensors. The derived confidence value is indicative of the association between a wireless sensor of the plurality and the monitored patient.

DETAILED DISCLOSURE

Figure 1:
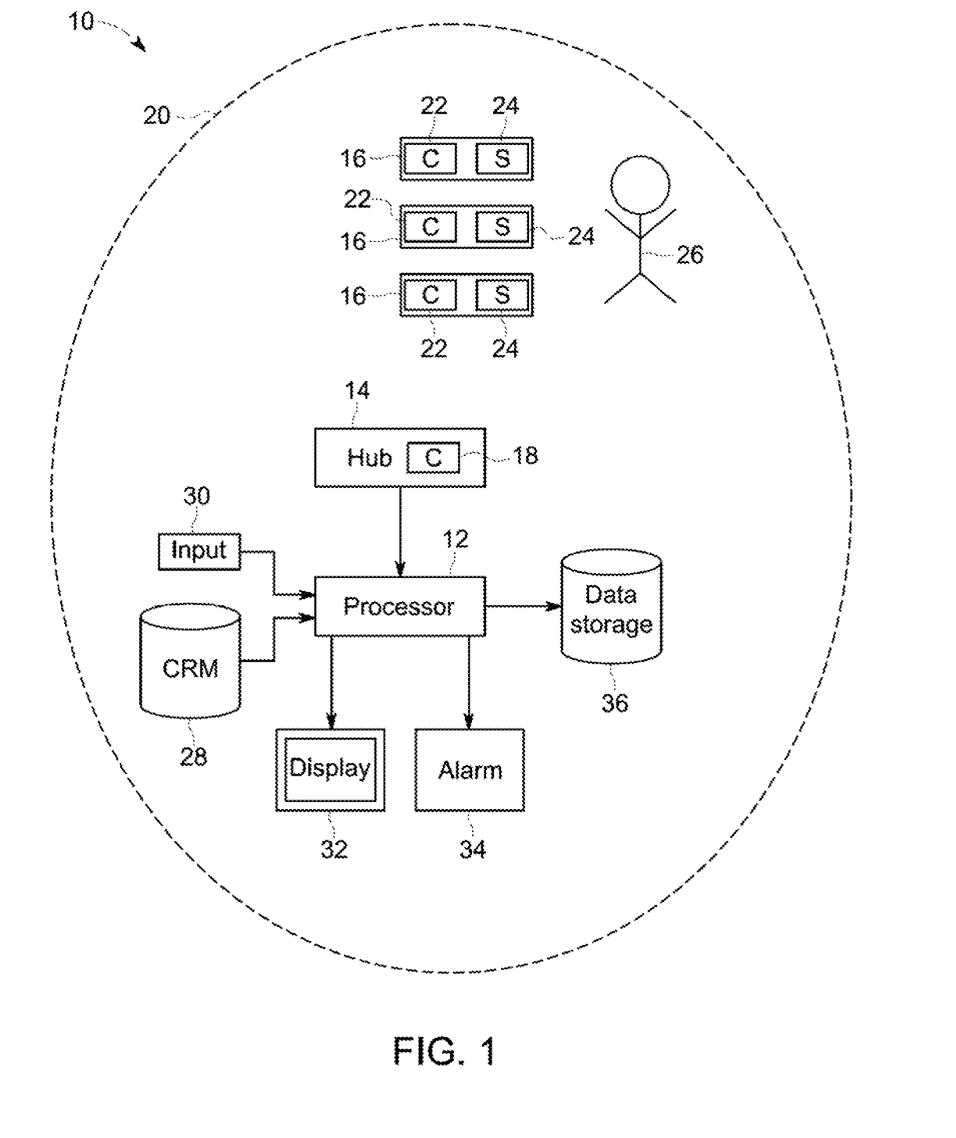
FIG. 1 is a schematic diagram of an exemplary embodiment of a wireless system.

FIG. 1 is a schematic diagram of a wireless system 10. The wireless system 10 includes a processor 12 that is configured in the manner as disclosed herein to receive a plurality of signals acquired by the wireless system 10 and evaluate the signals. The wireless system 10 further includes a hub 14 that is configured to communicate both with the processor 12 and with a plurality of peripheral electronic devices 16. It will be understood that in embodiments, the hub 14 may be an independent device that is communicatively connected to the processor 12, while in other embodiments the hub 14 may be integrated into a single device with the processor 12.

The hub 14 includes a wireless communication system 18 that exemplarily creates a communication area or range 20 within which the hub 14 may be communicatively connected with one or more of the peripheral electronic devices 16 which similarly may comprise a wireless communication system 22. It will be understood that the wireless communication systems 18, 22 respectively of the hub 14 and the peripheral electronic devices 16 will be communicatively compatible and in an embodiment are radio frequency (RF) wireless communication devices. However, it will be understood that in alternative embodiments, the wireless communication systems 18, 22 may include optical, magnetic, ultrasound, visible light, infrared, or other forms of wireless communication systems.

While embodiments of the peripheral electronic devices 16 may include other components as described in further detail herein, each of the peripheral electronic devices 16 include at least one sensor 24 that is operable to acquire or measure at least one parameter or signal. In the present disclosure, the exemplary embodiment and application of a health care setting is used for descriptive purposes, although, it will be recognized that alternative embodiments of the systems and methods as disclosed herein may be used in conjunction with other applications in which a plurality of wireless peripheral electronic devices must be managed. Thus, in the exemplary embodiment given herein, the sensors 24 may be physiological sensors that are configured to acquire physiological data from a patient to be monitored 26. In non-limiting embodiments, the sensors 24 may include heart rate, pulse rate, temperature, electrocardiogram (ECG), blood pressure (e.g. NIBP), respiration, physical movement, electroencephalogram (EEG) and others as may be recognized by a person of ordinary skill in the art.

In embodiments, the sensors of the peripheral electronic devices measure or otherwise acquire at least one physiological parameter from the patient 26. The wireless communication system 22 of the peripheral electronic devices works with the wireless communication system 18 of the hub 14 to wirelessly transmit the acquired physiological data through the hub 14 to the processor 12.

The processor 12 is connected to at least one computer readable medium 28. In embodiments, the processor executes computer readable code stored on the computer readable medium 28 as software and firmware. The execution of the computer readable code causes the processor 12 to operate in a manner such as to carry out the operations and functions as described herein. In an exemplary embodiment, the computer readable medium 28 is an integral part of the processor 12.

In still further embodiments, the processor is communicatively connected to at the least one computer readable medium 28. Data is stored on the computer readable medium 28 such data may include information regarding system attributes as described in further detail herein, association attributes as described herein, particular combinations of association attributes as may be used depending upon the patient, the peripheral electronic devices used, or the patient diagnosis etc. as will be described in further detail herein, and/or a weight or priority assigned to one or more of the association attributes.

An input device 30 is further connected to the processor 12 wherein by a technician can enter information including information regarding the patient to be monitored, the peripheral electronic devices used, the physiological condition of the patient, the association attributes to be used in evaluation of the association between the peripheral electronic devices, or a weighting to be used in evaluating such association attributes. In some embodiments as disclosed herein, the input device 30 may be used by the clinician or technician to initially register each of the peripheral electronic devices 16 to the patient to be monitored 26. This initial registration may include the use of a bar code scanner or entering some other type of identifying information from the peripheral electronic device or the execution of a registration process carried out by the wireless communication system 18, 22 of the peripheral electronic devices 16 and the hub 14, respectively.

The processor 12 further operates a graphical display 32 that visually presents an indication of the association status or a derived confidence value indicative of the association between each of the peripheral electronic devices and the monitored patient. The graphical display 32 operates to present such information in a graphical user interface (GUI) which may be configured in a variety of manners to visually convey this information. In embodiments, the graphical display 32 may be a flat panel display or may be a display associated with a laptop or tablet computer, or a display of a mobile device. In still further embodiments, the display 32 may have touch sensitive capabilities and as such operate as both the display 32 as well as the input device 30. In still further embodiments, the display 32 may further be operated by the processor 12 to present some or all of the physiological data acquired from the monitored patient by the plurality of peripheral electronic devices 16.

The processor 12 is further connected to an alarm 34. The alarm 34 may be an audible or visual alarm that produces an alert indicative of the association between each of the peripheral electronic devices and the monitored patient. In an embodiment, the alarm 34 may only provide an indication when the association between a peripheral electronic device and the monitored patient falls below a predetermined threshold as determined by the processor 12. The alarm may include a light indicator such as an LED; however, in alternative embodiments, the alarm 34 may be generated sound or a textual message sent to one or more care providers through text messaging, e-mail or other known communication platforms.

The processor 12 is further connected to data storage 36 wherein the data storage 36 may be located on a computer readable medium that is either local or remote from the processor 12. Thus, the data storage 36 may be communicatively connected to the processor 12 through a local hospital intranet or a wide area network exemplarily over the Internet. In one embodiment, the data storage 36 is exemplarily an electronic medical record (EMR) of the monitored patient and the processor 12 stores both the acquired physiological data received from the plurality of peripheral electronic devices and the association status or confidence value determined for each of the peripheral devices by the processor 12 in the data storage 36 in conjunction with the acquired physiological data.

Figure 2:
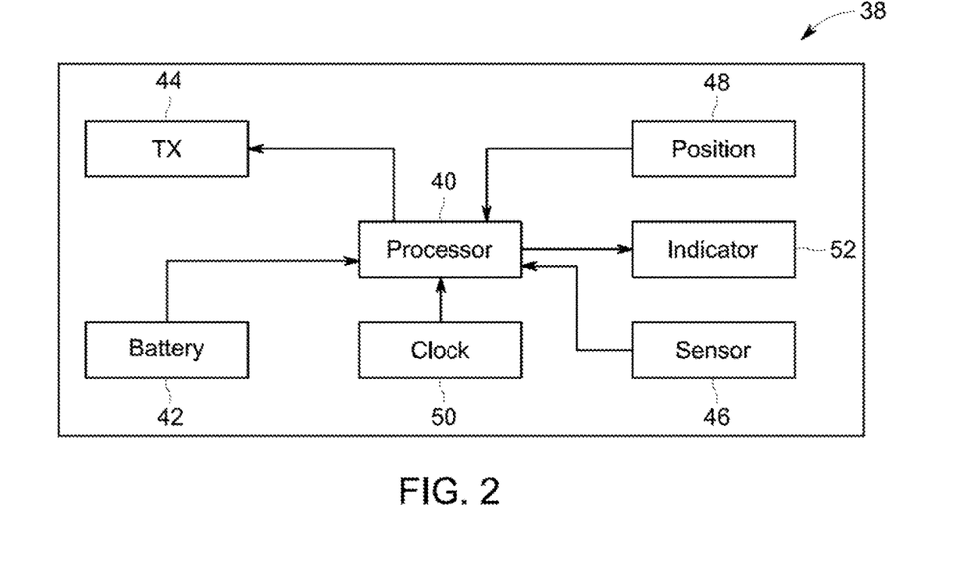
FIG. 2 is a schematic diagram of an exemplary embodiment of a peripheral electronic device.

FIG. 2 depicts a more detailed exemplary embodiment of a peripheral electronic device 38 such as may be used in conjunction with the wireless system 10 depicted in FIG. 1. The peripheral electronic device 38 includes a processor 40 that executes software or firmware stored at the processor 40 in order to carry out the functions as described in further detail herein. The peripheral electronic device 38 further includes a battery 42 that provides power to the processor 40 and other components of the peripheral electronic device requiring energization, either directly or indirectly from the battery 42. In an embodiment, the peripheral electronic device 38 may be constructed such that the battery 42 is replaceable or rechargeable. In such embodiments, the peripheral electronic device 38 may be configured to be reused and the battery replaced or recharged in order to extend the life of the peripheral electronic device. In other embodiments, the peripheral electronic device 38 may be disposable after the power is drained from the battery 42. Depending upon such embodiments, the processor 40 may monitor either the remaining battery life, elapsed time or elapsed usage since battery replacement or recharge, battery output voltage, or other such measurement of remaining battery life.

As described above, the peripheral electronic device is configured to be secured to the patient to be monitored and to wirelessly transmit information through an interaction between a wireless communication system 18 of a hub 14, with a wireless communication system 22 of the peripheral electronic device 16 (FIG. 1). In the exemplary embodiment of FIG. 2 the peripheral electronic device 38 includes a transmitter 44 in order to broadcast or otherwise transmit information from the peripheral electronic device as described above, the transmitter 44 may include any of a variety of known communication transmitters, including, but not limited to radio frequency, infrared, visible light, or ultrasonic, or other known transmission implementations.

The peripheral electronic device 38 is configured with a sensor 46. The sensor 46 is configured to acquire or otherwise measure a physiological parameter from the patient. Non-limiting examples of physiological parameters that may be measured or acquired, include biopotentials such as electrocardiogram (ECG), electromyogram (EMG), and electroencephalogram (EEG). The sensor 46 may also be configured to acquire other physiological parameters such a heart rate, oxygen saturation ($SPO_2$), blood pressure, such as acquired by noninvasive blood pressure (NIBP) monitoring, respiration rate, motion detection, or temperature. However, these are merely exemplary of the types of sensors that may be incorporated into the peripheral electronic device 38 and are not intended to be limiting.

Embodiments of the peripheral electronic device 38 may further include a position detector 48. In an exemplary embodiment, the position detector 48 may be a global positioning system (GPS) detector. The position detector 48 further provides the location of the peripheral electronic device 38 and can be transmitted by the transmitter 44 along with the physiological data collected by the sensor 46.

The peripheral electronic device 38 may further include a clock 50 where the clock 50 may be a separate component found in the peripheral electronic device 38, or may be an integral component associated with the processor 40. In embodiments, the clock 50 can operate such as to measure an elapsed time since initial registration of the peripheral electronic device 16 with the processor 12 (FIG. 1) to the monitored patient as described above. In an alternative embodiment, the clock 50 may be used to measure the operational time since the last battery replacement or recharge as also discussed above.

The peripheral electronic device 38 further may include an indicator 52 connected to the processor 40. In embodiments, for notification purposes, the indicator 52 may be a noise making device, an LED or other visual device, or a tactile device such as a vibration unit for notifying a clinician or technician of the association status of the peripheral electronic device 38 with the monitored patient through sound, light, or tactile methods.

Figure 3:
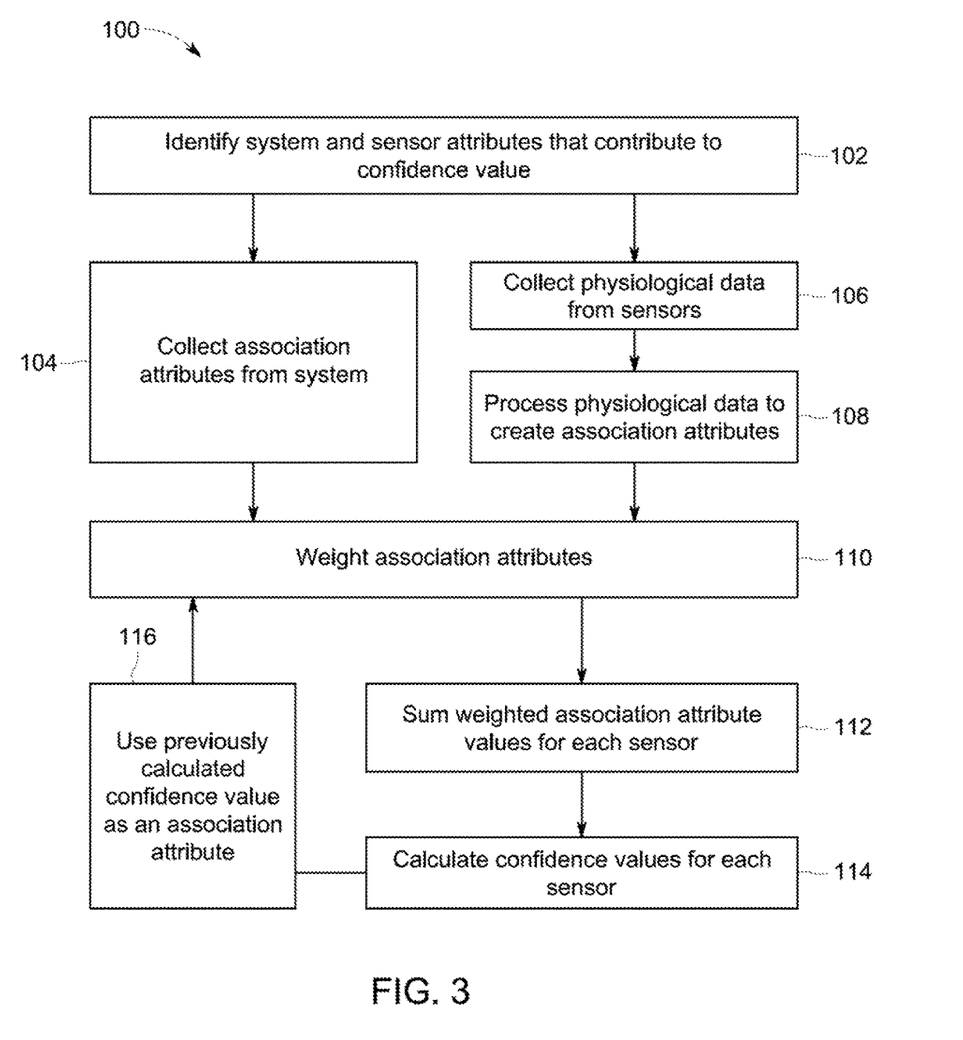
FIG. 3 is a flow chart that depicts an exemplary embodiment of a method of evaluating an association between a wireless sensor and a monitored patient.

FIG. 3 is a flow chart that depicts an exemplary embodiment of a method 100 of evaluating an association between a wireless sensor and a monitored patient. The exemplary embodiment of the method 100 begins at 102 wherein at least one system and sensor attributes that contribute to the confidence value are identified. Depending upon the sensor itself, the type of wireless communication system used by the sensor, and the components available in the sensor (e.g. clock, position device, as described above), certain system and sensor attributes as described in further detail herein may be more relevant or applicable in calculating the confidence value. Alternatively, some system and sensor attributes may not be available due to the constraints of the sensors and system themselves. As such, for any given sensor, a subset of the overall set of possible association attributes will exist.

At 104 system attributes are collected from the system. The system attributes are values and conditions that are related to the association of the sensor to the monitored patient, but are a part of the wireless system rather than physiological data acquired from the patient. Examples of association attributes that are collected from the system at 104 can include length of time, registration of a sensor to a patient, RF signal strength, activity types, numbers of communication errors, battery state or condition, known operation lifetime of the peripheral electronic device, a location, exemplarily a GPS location, a proximity beacon, elapsed time on the patient, identified instances of sensor disconnection from the patient, movement of the peripheral electronic device, or a location of an accessory or other device associated with the patient; however, these are merely exemplary of the types of association attributes that would be collected from the system. In an embodiment, exemplary association attribute values for such association attributes may include a numerical representation of RF signal, a medical association confidence based upon the length of time from the peripheral electronic device has been registered to the monitored patient. An association attribute value may be a numerical representation of a confidence that the peripheral electronic device is associated with the patient to be monitored. For example, if the RF signal strength of one peripheral electronic devices is noticeably weaker or stronger than those of other peripheral electronic devices registered to the same patient, this may indicate low confidence while congruency between all RF signals of the peripheral electronic devices registered to the same patient may be a sign of increased confidence. Similarly, as the length of time since the initial registration of the peripheral electronic device, or length of time since a clinician's physical verification of connection of the peripheral electronic device to the monitored patient gets longer, the confidence in the association decreases. Similarly, if a peripheral electronic device extends beyond an expected life, battery power, battery life, or recommended replacement time, these may all be indications of a lowered confidence than the association status. In other examples, if a sensor experiences a large number of communication errors or is in a location apart from other peripheral electronic devices registered to the monitored patient, these may be indicative of a reduced confidence in the association status of the peripheral electronic device.

At 106 physiological data is collected from the sensors of the peripheral electronic devices and transmitted to the processor as described above through the wireless system. As further described above, a variety of physiological data may be selected from the sensors associated to each patient. Depending upon the diagnosis and treatment being received by the patient, the patient may be monitored to acquire various physiological data.

At 108 the acquired physiological data is processed to create association attributes, and specifically to calculate association attribute values based upon the obtained physiological data. At 108, the association attributes acquired from the physiological data may include, but are not limited to heart rate, pulse rate, temperature, ECG waveform characteristics, pressure waveform characteristics, respiration rate, physical movement, EEG waveform characteristics, and others as will be recognized by a person of ordinary skill in the art. Similar as to that described above with respect to association attributes collected from the system at 104, the association attributes created from the physiological data may include such association attribute values that are representative of a confidence in the association status between an peripheral electronic device and the monitored patient. Such association attribute values are a measure of the coincidence or congruity between physiological data acquired between sensors of peripheral electronic devices in the plurality of peripheral electronic devices.

In one example, a plurality of ECG leads may be acquired by separate peripheral electronic devices and an ECG signal, waveform characteristic, or heart rate as indicated by each of the ECG leads are compared to determine whether each ECG signal is consistent or inconsistent with the other leads. If the ECG signal obtained from one of the peripheral electronic devices is inconsistent with the other ECG signals from the peripheral electronic devices associated with the monitored patient, then that peripheral electronic device will have a lower association attribute value to reflect the reduced confidence that that peripheral electronic device is associated with the monitored patient. Similar comparisons may be made across physiological parameters, exemplarily, heart rate as determined through ECG signals acquired by peripheral electronic devices, and $SPO_2$ peripheral electronic devices and an NIBP peripheral electronic device may all be compared to evaluate the consistency or inconsistency of the heart rates between each of these peripheral electronic devices to evaluate their association to the monitored patient.

In still further embodiment, one physiological parameter measured by a sensor of one of the peripheral electronic devices may produce a known artifact in the signal acquired by a sensor of a peripheral electronic device configured to acquire another physiological parameter. Exemplarily, a known cardiac artifact may appear in any of a number of physiological parameter signals, including, but not limited to a respiration monitor, EEG waveform, or EMG waveform. Similarly, a respiration artifact may be known to be present in an acquired ECG signal. In an alternative embodiment, the monitored physiological data, e.g. heart rate, as acquired from an ECG signal is compared to the known cardiac artifact in the physiological data acquired by another peripheral electronic device and an association attribute value created reflective of the consistency or inconsistency, of this comparison between the physiological data of the peripheral electronic devices. In a still further embodiment, one or more of the peripheral electronic devices may comprise a motion detector, such as an accelerometer. Detected motion signals from that peripheral electronic device can be compared to motion artifacts found in physiological data acquired by similarly located peripheral electronic devices.

At 110 the association attributes are weighted. A weighting criteria is determined based upon the strength of the overall attribute as well as the total number of attributes available in a subset of available association attributes. Weighting criteria may also be further determined based upon the known values of the association attribute. As noted above, not all association attributes may be used or available in all instances. Specifically, based upon the types of sensors or types of peripheral electronic devices and the types and amount of physiological data collected, only a subset of the possible association attributes will be available and the relative strength of the association attributes in determining an association status between a peripheral electronic device and a monitored patient may be considered in weighting the association attribute. For example, an association attribute such as an elapsed time since initial registration may be heavily weighted if the elapsed time is short, but may receive a lesser weighting as the elapsed time lengthens. In an embodiment, the weighting may again increase if the elapsed time exceeds an expected procedure or peripheral electronic device duration or usage. It is to be noted that in some embodiments only physiological data based association attributes may be used while in other embodiments a combination of system association attributes and physiological association attributes may be used. It is possible that the number of attributes changes and the weighting criteria changes during a single device-patient association session. As will be discussed in further detail herein, embodiments of the method 100 may be repeated periodically in order to produce an updated evaluation of the association between the peripheral electronic devices and the monitored patient and the weighting of the association attributes may change from cycle to cycle. These changes may be due to the addition or subtraction of peripheral electronic devices, length of time elapsing between evaluation cycles.

At 112 the weighted association attribute values are summed on a sensor by sensor basis. This summation may produce a raw indication of the association between each of the individual peripheral electronic devices of the plurality and the patient to be monitored by those peripheral electronic devices. At 114 a confidence value is calculated for each peripheral electronic device based upon the summed weighted association attribute values. The confidence value calculated at 114 may exemplarily be a normalized value of the summed weighted association attribute values. In an alternative embodiment, the confidence value may be normalized on an S curve. Alternatively, an association status may be determined from the summed weighted association attribute values, exemplarily into categories of high, medium, and low association status.

In embodiments, as mentioned above, the association status and confidence in the association between a peripheral electronic device and the monitored patient may be periodically recalculated such as to update these determinations. In one embodiment, once a confidence value has been calculated at 114 this previously calculated confidence value may be used at 116 as another association attribute that is weighted and incorporated into the determination at 110.

Figure 4:
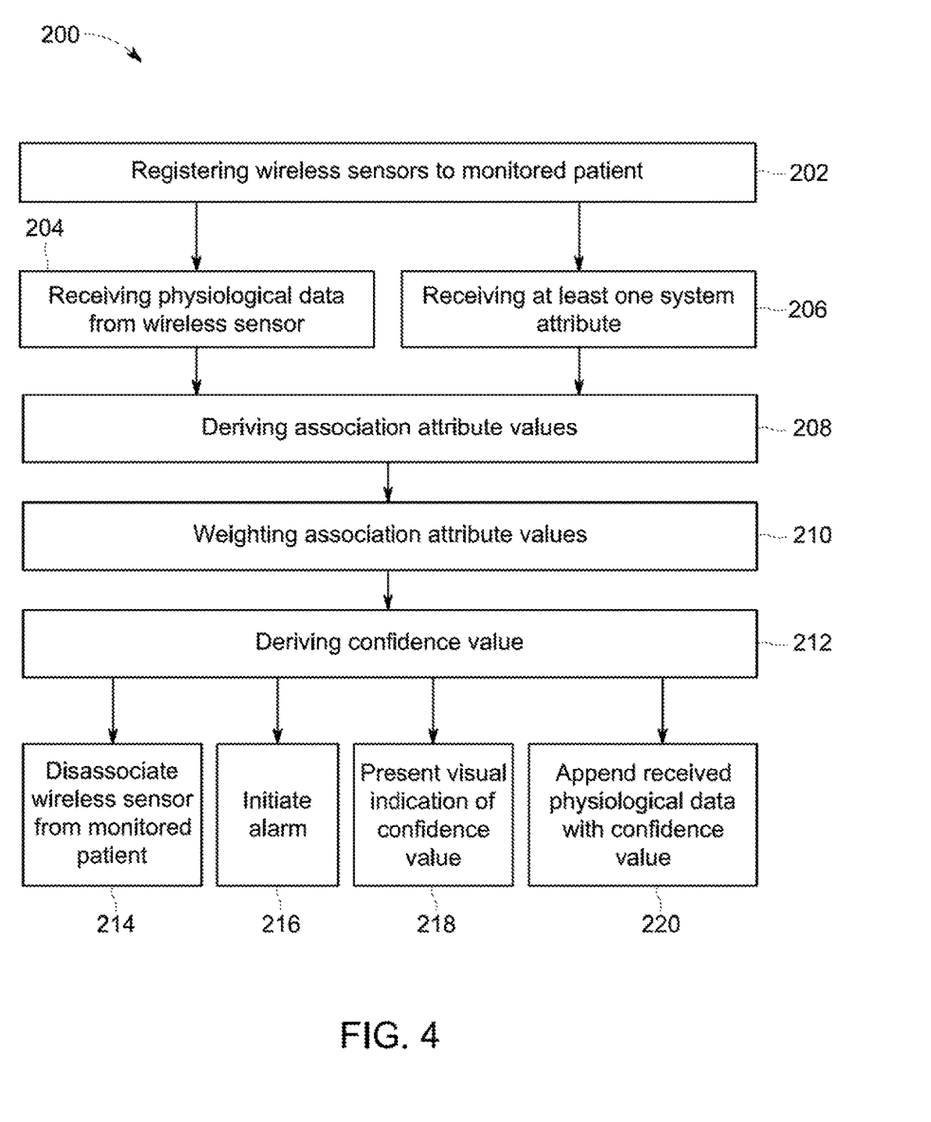
FIG. 4 is a flow chart that depicts an alternative exemplary embodiment of a method of evaluating an association between a wireless sensor and a monitored patient.

FIG. 4 is a flow chart that depicts an exemplary embodiment of a method 200 of evaluation an association between each of a plurality of wireless sensors and a monitored patient. The method 200 may exemplarily be carried out by an embodiment of the wireless system 10 as described above with respect to FIG. 1. At 202, each wireless sensor of the plurality of wireless sensors is registered to a monitored patient. It will be recognized that in the description herein, the wireless sensors registered at 202, may be a part of a peripheral electronic device that is configured to be secured to a patient and to transmit physiological data acquired by the wireless sensor to a processor in the wireless system. As described above, the wireless sensors may be registered by one or more clinician or technician inputs into the wireless system in order to provide an initial association between each of the plurality of wireless sensors and the patient to be monitored. Once the wireless sensors are registered and secured to the monitored patient, the processor may begin to receive physiological data as acquired by the wireless sensors through the wireless system. The processor can begin to calculate at least one association attribute value based upon the received physiological data.

The processor may also receive at least one system attribute at 206 from another component of the wireless system, which may be, as described above, any of a variety of system attributes including, but not limited to an elapsed time that a wireless sensor is associated to a patient, an elapsed time that a sensor is off of a patient, an RF signal strength, an activity type, a number of communication errors, a battery state, a sensor life, a sensor location (e.g. GPS), an accessory status, or a proximity beacon.

At 208, the processor derives association attribute values based upon the physiological data received at 204 and the at least one system attribute received at 206. The association attribute values may be derived in a number of ways, including those as described above with respect to FIG. 3.

Next, at 210 the association attribute values are weighted and at 212 a confidence value is derived for each of the wireless sensors registered to the monitored patient. The weighting of the association attribute values and the derivation of the confidence values from the weighted association attribute values are described in greater detail above with respect to FIG. 3.

In the method 200 a number of alternative responses or actions may be taken once the confidence value is derived at 212. In embodiments, it will be recognized that one or more of these responses may occur simultaneously, or sequentially, or that other types of responses are also contemplated herein.

At 214, if the confidence value derived at 212 is below a predetermined threshold, the wireless sensor may be disassociated from the monitored patient. In such an embodiment, the physiological data obtained by the wireless sensor may still be temporarily stored, but may not be immediately entered into the patient's electronic medical record, or presented on a graphical display of the patient's physiological data. If, at a later time, the wireless sensor is verified to have been associated with the monitored patient at the time that the data was acquired, the physiological data may be restored to the patient's electronic medical record. In an alternative embodiment, once the wireless sensor is disassociated, the wireless system may no longer process or store the physiological data from the wireless sensor. Similarly, at 216, if the derived confidence value at 212 is determined to be below a predetermined threshold, an alarm, which may be a visual, audio, or tactile alarm is initiated to alert a clinician or technician of the reduced confidence in the association between the wireless sensor and the monitored patient. In an exemplary embodiment, there may be a plurality of allowed states or stages each defined by a threshold and set alarm stages or states may result in various alarm responses which escalate with the escalation of the determined alarm state or stage.

Figure 5:
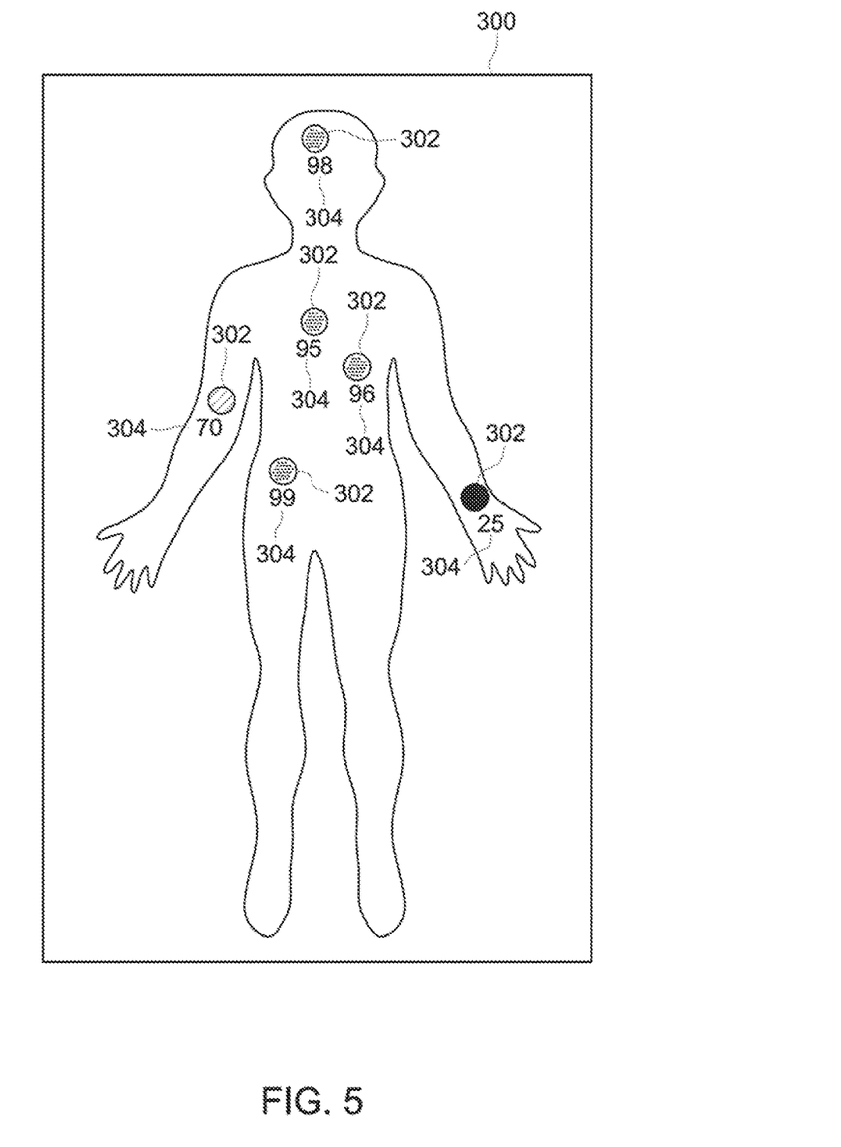
FIG. 5 depicts an exemplary embodiment of a graphical user interface in accordance with an exemplary embodiment.

At 218, regardless of the derived confidence value, a visual indication of the derived confidence value may be presented to a clinician or technician. This visual presentation may exemplarily be in a graphical user interface presented on a graphical display operated by the processor. FIG. 5 depicts an exemplary embodiment of a graphical user interface 300 that may be presented on a graphical display. The GUI 300 includes a plurality of sensor indicators 302. The sensor indicators 302 may generally identify the anatomical location of the wireless sensor on the monitored patient. In an exemplary embodiment, the sensor indicators 302 may be color coded to represent an association status of the sensor based upon the confidence value, such association status may exemplarily indicate a high, medium, or low association between the wireless sensor and the monitored patient. The GUI 300 may further present the derived confidence value 304 associated with each of the wireless sensors. Thus, in embodiments such as that depicted in FIG. 5, a clinician or technician is presented with both a visual indication of a general association status as well as a more detailed confidence value indication.

Referring back to FIG. 4 at 220, once the confidence values for each wireless sensor are derived at 212, the received physiological data from each of the wireless sensors may be appended with the confidence value associated with the time interval in which the physiological data was acquired. This appended physiological data can then be stored, exemplarily at the monitored patient's EMR such that the appended physiological data can be later used in patient evaluation, diagnosis, or therapeutic decisions as an additional piece of information that is reflective of the quality or confidence that acquired physiological data was acquired by a wireless sensor that was actually associated with that patient.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A wireless system comprising:
a plurality of peripheral electronic devices each having a wireless communication system and a sensor, each sensor configured to measure physiological data of a monitored patient;
a hub having a wireless communication system, the hub in wireless communication with one or more of the peripheral electronic devices; and
a processor that first receives measured physiological data from the peripheral electronic devices and collects at least one system or sensor attribute value for each electronic device of the plurality of electronic devices, next calculates association attribute values by comparing the collected at least one system or sensor attribute value from each electronic device to the at least one system or sensor attribute values from the rest of the plurality of electronic devices, and then the processor establishes an association status between each of the peripheral electronic devices and the monitored patient based on the association attribute values.

2. The wireless system of claim 1, wherein the at least one system or sensor attribute value comprises a sensor attribute value derived from the measured physiological data.

3. The wireless system of claim 2, wherein the measured physiological data comprises at least one of heart rate data, pulse rate data, blood pressure data, respiration rate data, temperature data, electrocardiographic data, and electroencephalographic data.

4. The wireless system of claim 3, wherein the association attribute values reflect a similarity of the measured physiological data between each of the peripheral electronic devices.

5. The wireless system of claim 1, wherein the at least one system or sensor attribute value comprises a system attribute value.

6. The wireless system of claim 5, wherein the system attribute value is a value received by the processor from the sensor.

7. The wireless system of claim 5, wherein the system attribute value is a value created by the processor.

8. The wireless system of claim 5, wherein the system attribute value comprises at least one of an elapsed time since registration of the peripheral electronic devices to the monitored patient, a battery life of each of the peripheral electronic devices, an operation time of each of the peripheral electronic devices, communication errors between each of the peripheral electronic devices and the hub, a signal continuity from each of the peripheral electronic devices, and identified sensor disconnects for each of the peripheral electronic devices.

9. A wireless system comprising:
a plurality of peripheral electronic devices each having a wireless communication system and a sensor, the sensors configured to each obtain a signal out of a plurality of signals;
a hub having a wireless communication system, the hub in wireless communication with one or more of the plurality of peripheral electronic devices; and
a processor that first receives at least one input to register each of the plurality of peripheral electronic devices, the processor next receives the plurality of signals from the peripheral electronic devices and collects at least one system or sensor attribute value for each electronic device of the plurality of electronic devices, then calculates association attribute values by comparing the collected at least one system or sensor attribute value from each electronic device to the at least one system or sensor attribute values from the rest of the plurality of electronic devices, and further the processor calculates a confidence value indicative of an association status between a registration of each of the peripheral electronic devices and the at least one association attribute value.

10. The wireless system of claim 9, further comprising:
wherein each signal of the plurality of signals is physiological data and the sensors measure physiological data of a monitored patient;
wherein the at least one input registers each of the plurality of peripheral electronic devices to the monitored patient; and
wherein the confidence value is indicative of an association status between each of the peripheral electronic devices and the monitored patient.

11. The wireless system of claim 10, wherein the at least one system or sensor attribute value comprises a sensor attribute value derived from the physiological data from each of the peripheral electronic devices.

12. The wireless system of claim 11, wherein the association attribute values reflect a similarity of the measured physiological data between each of the peripheral electronic devices.

13. The wireless system of claim 12, wherein at least one signal of the plurality of signals received by the processor from the plurality of peripheral electronic devices comprises physiological data of at least one of heart rate data, pulse rate data, blood pressure data, an oxygen saturation data and at least one further signal of the plurality of signals received by the processor from the plurality of electronic devices comprises physiological data of at least another of heart rate data, pulse rate data, blood pressure data, an oxygen saturation data.

14. The wireless system of claim 10, wherein the processor further appends the received physiological data with the derived confidence value for the wireless sensor at the time of acquisition of the physiological data.

15. The wireless system of claim 9, wherein the at least one system or sensor attribute value comprises a system attribute value.

16. The wireless system of claim 15, wherein the system attribute value comprises at least one of an elapsed time since registration of the peripheral electronic devices, a battery life of each of the peripheral electronic devices, an operation time of each of the peripheral electronic devices, communication errors between each of the peripheral electronic devices and the hub, a signal continuity from each of the peripheral electronic devices, and identified sensor disconnects for each of the peripheral electronic devices.

17. The wireless system of claim 15, wherein the processor assigns initial weights to the association attribute values, the processor adjusts the initial weights according to received system attribute values and derives the confidence value further from the weighted association attribute values.

18. A method of evaluating an association between each of a plurality of wireless sensors configured to obtain physiological data and a monitored patient, the method comprising:
- registering the plurality of wireless sensors to the monitored patient with a processor configured to receive the physiological data from the plurality of wireless sensors through a hub having a wireless communication system in communication with one or more of the plurality of wireless sensors;
- receiving the physiological data at the processor from the plurality of wireless sensors;
- calculating at least one sensor attribute value as an association attribute value of a plurality of association attribute values by processing the received physiological data to compare the received physiological data from each of the plurality of wireless sensors to the physiological data received from the rest of the plurality of wireless sensors;
- receiving at least one system attribute value as a further association attribute value of the plurality of association attribute values;
- weighting each of the plurality of association attribute values;
- calculating a confidence value from the weighted plurality of association attribute values for each of the plurality of wireless sensors indicative of the association between a wireless sensor of the plurality and the monitored patient.

19. The method of claim 18, wherein the at least one system attribute value comprises a registration of the plurality of wireless sensors to the monitored patient and further comprises an elapsed time since registration of each of the plurality of wireless sensors to the monitored patient and further comprising:
- decreasing a weight given to the registration of the plurality of sensors to the monitored patient as the elapsed time since registration of each of the plurality of wireless sensors to the monitored patient increases.

20. The method of claim 18, wherein the response is selected from a group consisting of disassociating at least one wireless sensor from the monitored patient, initiating an alarm, presenting a visual indication of the derived confidence value on a graphical display, and appending the received physiological data with the derived confidence value for the wireless sensor at the time of acquisition of the physiological data.

* * * * *